(12) United States Patent
Gisler et al.

(10) Patent No.: US 10,577,596 B2
(45) Date of Patent: Mar. 3, 2020

(54) DEVICE FOR SEPARATION

(71) Applicant: Roche Molecular Systems, Inc., Pleasanton, CA (US)

(72) Inventors: Andreas Gisler, Thalwil (CH); Raphael Gut, Lucerne (CH); Thomas Meyer, Walchwil (CH); Marco Sangermano, Kriens (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 137 days.

(21) Appl. No.: 15/442,316

(22) Filed: Feb. 24, 2017

(65) Prior Publication Data

US 2017/0253870 A1    Sep. 7, 2017

(30) Foreign Application Priority Data

Mar. 2, 2016   (EP) .................................. 16158300

(51) Int. Cl.

| | |
|---|---|
| *C12N 15/10* | (2006.01) |
| *B03C 1/02* | (2006.01) |
| *C12Q 1/68* | (2018.01) |
| *B03C 1/01* | (2006.01) |
| *B01L 9/00* | (2006.01) |
| *C12Q 1/6806* | (2018.01) |
| *G01N 35/02* | (2006.01) |
| *G01N 35/00* | (2006.01) |

(52) U.S. Cl.
CPC .......... *C12N 15/1013* (2013.01); *B01L 9/523* (2013.01); *B01L 9/543* (2013.01); *B03C 1/01* (2013.01); *B03C 1/02* (2013.01); *C12Q 1/6806* (2013.01); *B01L 2400/043* (2013.01); *G01N 35/0098* (2013.01); *G01N 35/028* (2013.01)

(58) Field of Classification Search
CPC ..... C12N 15/1013; B01L 9/523; B01L 9/543; B03C 1/01; B03C 1/02
See application file for complete search history.

(56) References Cited

U.S. PATENT DOCUMENTS

| | | | |
|---|---|---|---|
| 8,404,489 B2 | 3/2013 | Akashi et al. | |
| 2002/0007054 A1* | 1/2002 | Sakurai | C12N 15/1006 536/25.41 |
| 2010/0027261 A1 | 2/2010 | Yashima et al. | |
| 2010/0272614 A1 | 10/2010 | Bulow et al. | |
| 2010/0284864 A1* | 11/2010 | Holenstein | B01L 3/5085 422/511 |

(Continued)

FOREIGN PATENT DOCUMENTS

| | | |
|---|---|---|
| EP | 0884104 B1 | 12/1998 |
| EP | 1839756 A1 | 10/2007 |
| EP | 2752671 A2 | 7/2014 |

OTHER PUBLICATIONS

EP search report for EP 16158300.0.

*Primary Examiner* — Krishnan S Menon
*Assistant Examiner* — Dwan A Gerido
(74) *Attorney, Agent, or Firm* — Eric Grant Lee

(57) ABSTRACT

A device comprising a support part is disclosed. The support part is configured to receive a tip holder, a liquid waste container and a multiwell plate. The multiwell plate comprises at least one row of vessels which comprise a closed bottom and an open top. A method of removing liquid waste during magnetic separation using such a device is also disclosed.

11 Claims, 12 Drawing Sheets

(56) References Cited

U.S. PATENT DOCUMENTS

| | | | |
|---|---|---|---|
| 2012/0309104 A1* | 12/2012 | Uematsu | G01N 35/0098 436/174 |
| 2013/0043191 A1* | 2/2013 | Park | C12M 33/06 210/695 |
| 2013/0137109 A1 | 5/2013 | Wilson et al. | |

* cited by examiner

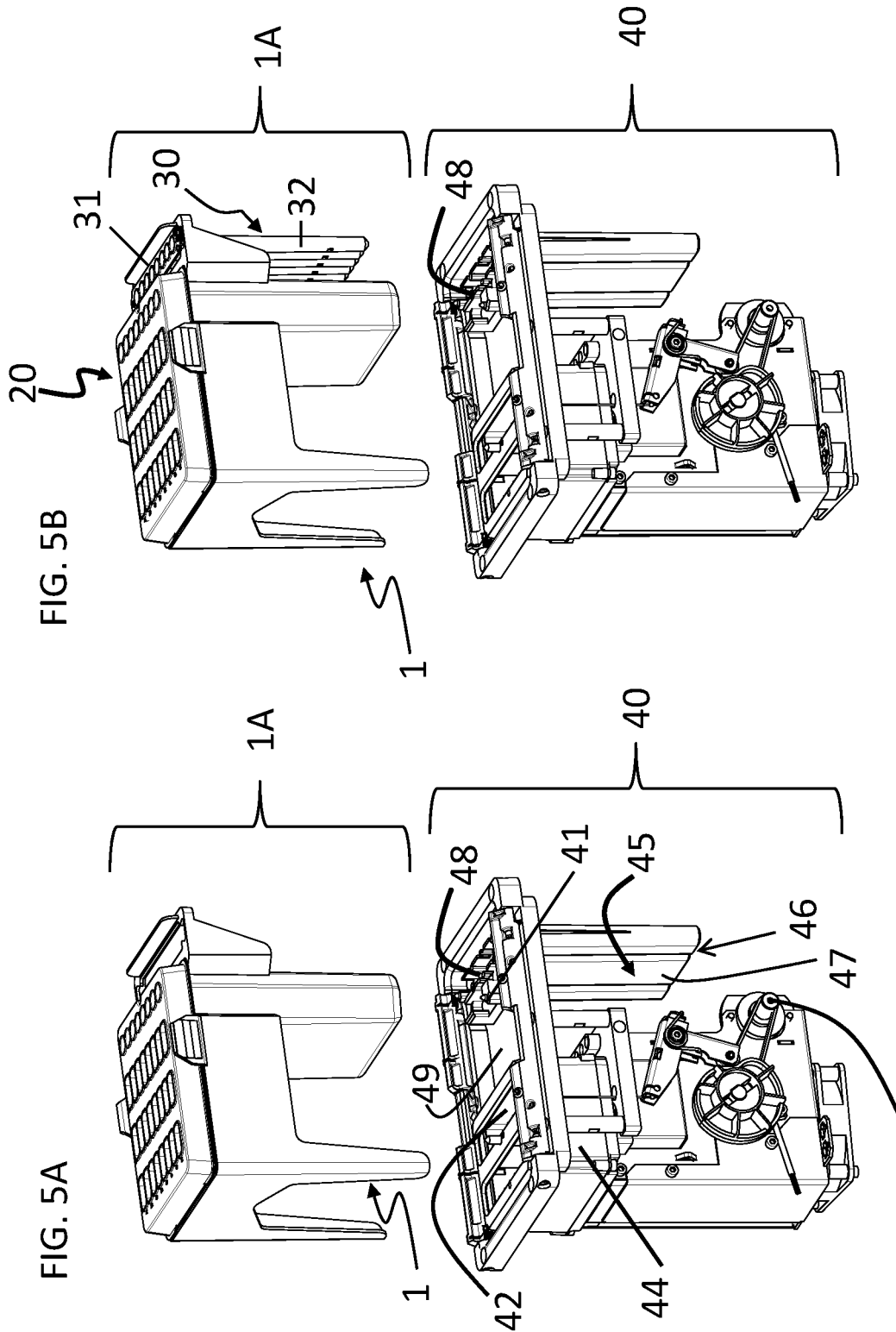

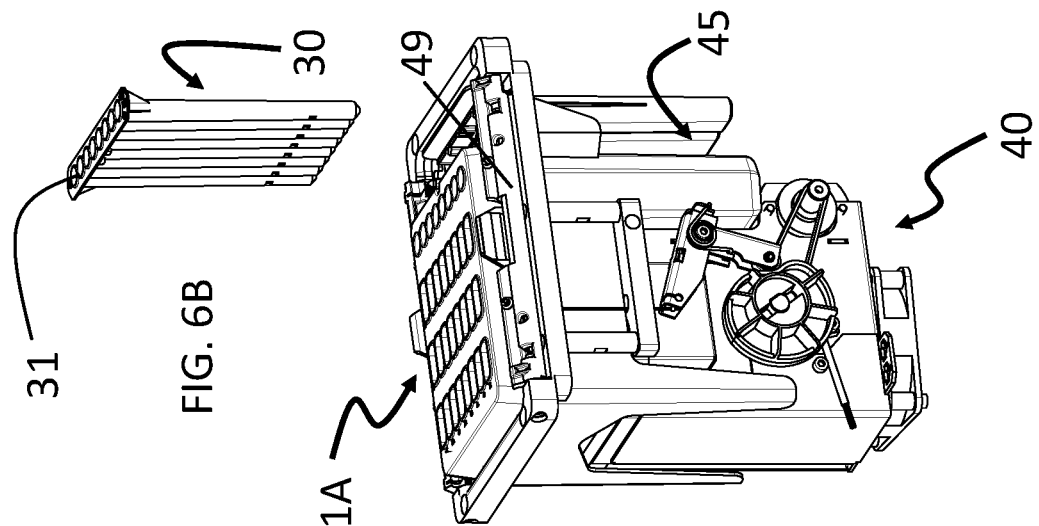
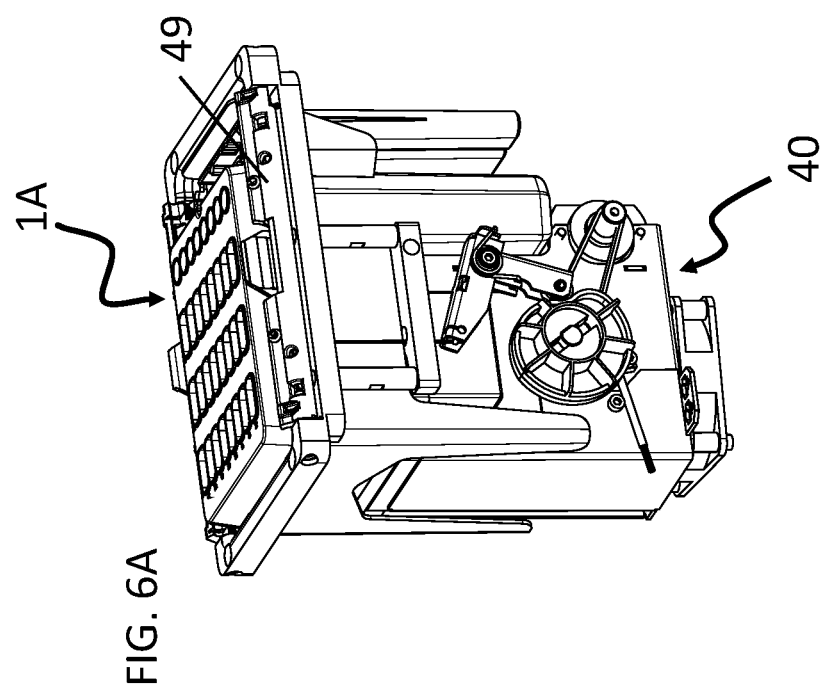

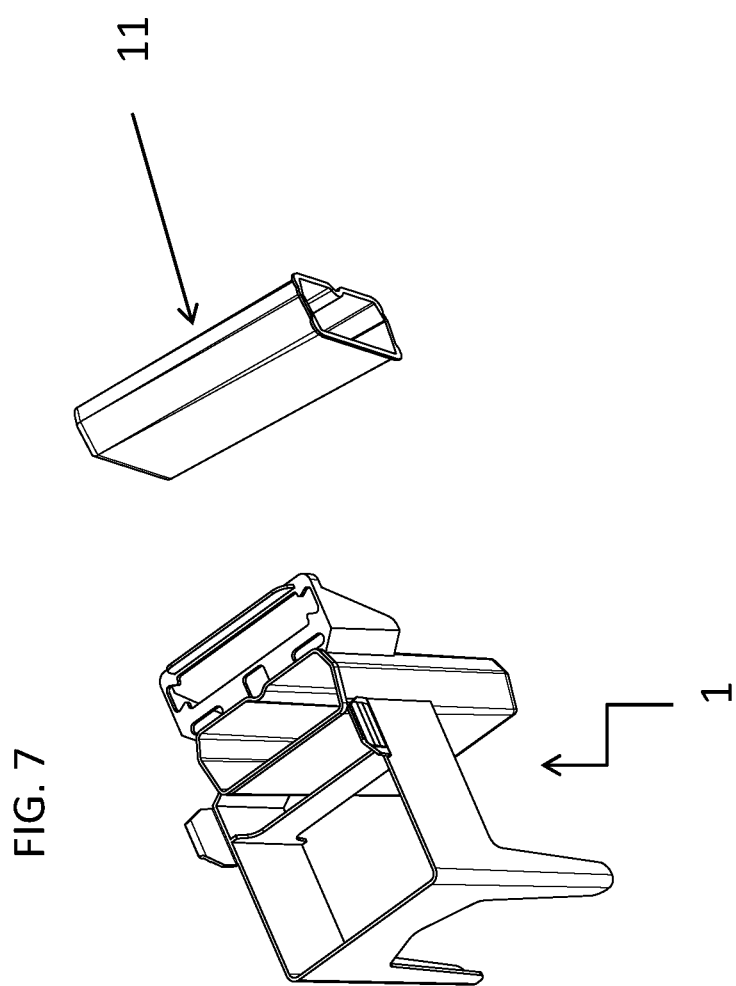

DEVICE FOR SEPARATION

CROSS-REFERENCE TO RELATED APPLICATION

The present application claims the benefit of priority from EP Application No. 16158300.0, filed on Mar. 2, 2016, the content of which is incorporated herein by reference in its entirety.

BACKGROUND

The present disclosure relates to devices, systems and methods for separating an analyte from a liquid sample. Separation of analytes from liquid samples is an important step in the preparation of samples for subsequent analysis to detect the presence or absence, or to quantitate analytes in liquid or liquified samples. Different systems exist for separating analytes from other components present in liquid samples. One such separation system is based on binding of analytes to magnetic or magnetized particles. The bound analyte can be separated from the liquid non-bound components by applying a magnetic field in a magnetic separation station. For lysis and/or elution of the bound analyte, heating may be further required.

In conventional systems, heating stations and separation stations comprise a receiving part for vessels which contain the liquid sample. Such vessels are commonly provided in single vessels or in integrally formed multiwell plates. The vessels are placed in the receiving part of the station and are removed again after separation and transfer of the separated analyte to a different vessel. After removal from the receiving part of the separation station, the vessels or multiwell plates are discarded. In semi-automated systems, the consumables are commonly loaded and unloaded manually on the separation station. Such manual loading and unloading is cumbersome and prone to user errors. Not all consumables can be surveyed (e.g. by barcode reading) to ensure their presence and proper use.

The present disclosure provides a new concept of assembling different consumables required for separation of an analyte in a magnetic separation station on a re-usable support part which can be reliably loaded and unloaded manually.

SUMMARY

The present disclosure relates to a device comprising a support part. The support part is configured to receive a tip holder, a liquid waste container and a multiwell plate. The multiwell plate comprises at least one row of vessels which comprise a closed bottom and an open top.

Also provided is a multi-part device comprising a device, said device comprising a support part, said support part being configured to receive a tip holder, a liquid waste container and a multiwell plate. The multiwell plate comprises at least one row of vessels and one row of openings. The vessels comprise a closed bottom and an open top, and the openings are aligned with the liquid waste container when said liquid waste container and the multiwell plate are mounted on said support. The multi-part device further comprises a tip holder, a multiwell plate and a liquid waste container, each being configured to be received by said support part.

The present disclosure further relates to a method of removing liquid waste during magnetic separation of an analyte, comprising the steps of:

providing a device as described herein, a liquid waste container and a multiwell plate comprising liquid samples mounted on said device to a magnetic separation station;

providing magnetic particles to said sample;

binding said analyte, if present in said sample, to said magnetic particles;

separating said magnetic particles and said liquid samples using magnetic separation; and removing said liquid sample by transferring said liquid sample to said liquid waste container using a liquid transfer system, thereby removing liquid waste during magnetic separation.

BRIEF DESCRIPTION OF THE FIGURES

FIG. 1A illustrates the elements of the support part and FIGS. 1B-1D illustrate different states of loading a liquid waste container (11) on the device (1).

FIGS. 5A and 5B show the multi-part device (1A). In FIG. 5A, the device is loaded with the liquid waste container (11) and multiwell plate (20), and in FIG. 5B, the device is loaded with tip holder (30) comprising tip holder vessels (32) and tips (31).

FIGS. 6A to 6D show different stages of loading of the multi-part device (1A) into the separation and incubation station (40).

FIG. 7 shows the device 1 after discarding the multiwell plate (20) and tip holder (30).

DETAILED DESCRIPTION

Figure 1A:
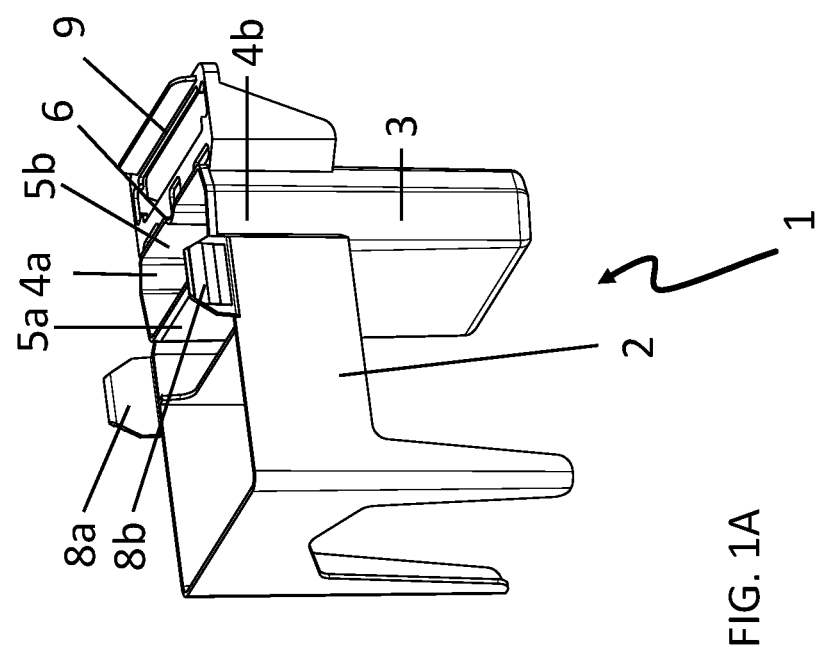
FIGS. 1A-1D show an embodiment of a device as described herein.

The present disclosure relates to a device comprising a support part. The support part is configured to receive a tip holder, a liquid waste container and a multiwell plate. The multiwell plate comprises at least one row of vessels which comprise a closed bottom and an open top, and one row of openings. The openings are aligned with the liquid waste container when said liquid waste container and said multiwell plate are mounted on said support.

One advantage of this device is that it permits the user to reliably load and unload consumables such as tips, liquid waste containers and multiwell plates on a separation station, because all consumables and the liquid waste are loaded or removed simply by loading or removing the device.

In one embodiment, the tip holder comprises one row of individually formed tip holder vessels configured to receive pipette tips, wherein said rows of vessels, said row of openings and said tip holder comprise an equal number of vessels/openings/tip holder vessels.

In one further embodiment, said vessels, openings and tip holder vessels are aligned.

In one embodiment, the liquid waste container has opposing long side walls and opposing short side walls which encompass an inner volume, and wherein said liquid waste container comprises a closed bottom and an open top.

In a more specific embodiment, one of said long side walls comprises a notch. This notch permits alignment with a ridge in the support part and with a ridge and hole in the multiwell plate. The notch, the ridges and the hole allow alignment with a pin present on the separation station. This ensures proper loading of the device comprising the support part and multiwell plate on the separation station.

In one embodiment, the support part comprises an enclosure, said enclosure being configured to receive the liquid waste container. In a specific embodiment, the enclosure comprises opposing short side walls and two opposing long side walls. In a further specific embodiment, one of said long side walls comprises a ridge. The ridge is configured to align with the notch of one of the long side walls of the liquid waste container.

In one embodiment, the enclosure comprises a closed bottom and an open top.

In one embodiment, the device comprises two handles arranged on two opposing sides of said device.

In one embodiment, the device is manufactured as one single part. Further, the device may be integrally formed, i.e., the device cannot be reversibly disassembled without being destroyed.

In one embodiment, the device is made of plastic.

In one embodiment, the device comprises an extension configured to receive a barcode.

In one embodiment, the device as described hereinbefore comprises, along one short side wall, the enclosure configured to receive the liquid waste container, and at least two legs, wherein the legs are located on the corners of the short side wall opposite the liquid waste container. The length of the legs and the liquid waste container is configured to permit the device to stand on a surface. This ensures a safe stand of the device. This permits the user to place the device on a trolley or other surface after unloading following separation, thus avoiding contamination of the surface before the consumables are discarded and the liquid waste emptied.

The present disclosure also relates to a multi-part device comprising a device, said device comprising a support part, said support part being configured to receive a tip holder, a liquid waste container and a multiwell plate, wherein said multiwell plate comprises at least one row of vessels and one row of openings, wherein said vessels comprise a closed bottom and an open top, and said openings are aligned with the liquid waste container when said liquid waste container and said multiwell plate are mounted on said support part; said multi-part device further comprising a tip holder, a multiwell plate and a liquid waste container, each being configured to be received by said support part.

In one embodiment, the multiwell plate comprises one row of openings. The openings are aligned with the liquid waste container when said liquid waste container and said multiwell plate are mounted on said support. In a further embodiment, the number of openings is the same as the number of vessels of at least one row of vessels of the multiwell plate.

In one embodiment, the openings are located above the liquid waste container when the liquid waste container and the multiwell plate are mounted on the support. In a further embodiment, the openings are formed as funnels on the bottom side of said base, and wherein said funnels are extending into said liquid waste container. This prevents contamination of the device or instrument or system by liquid waste.

Within the meaning of the present disclosure, it is understood that the use of the term "device" alone relates to the device as described herein. The term "multi-part device" relates to a device which comprises multiple separate parts. It does not relate to the "device" alone. However, it comprises the "device". Thus, the term "device" only relates to the multi-part device if the term is immediately preceded by the term "multi-part". If it is not immediately preceded by the term "multipart", then the term "device" only relates to the device comprising the support part, but without a tip holder, a multiwell plate and a liquid waste container.

In one embodiment of the multi-part device, the tip holder comprises one row of individually formed tip holder vessels configured to receive pipette tips. Each row of vessels, the row of openings and the tip holder comprise an equal number of vessels/openings/tip holder vessels. In a further embodiment, the vessels, openings and tip holder vessels are aligned. This permits easy liquid transfer using a multipipetting device. The tip holder is configured to fit into the tip holder receiving part of the support part of the device herein described. Multipipetting devices are well known in the art. Multipipetting devices engage disposable pipette tips and transfer liquids by aspirating liquids into the disposable tip and then dispensing the liquid again.

In one embodiment of the multi-part device, the liquid waste container has opposing long side walls and opposing short side walls which encompass an inner volume, and wherein said liquid waste container comprises a closed bottom and an open top.

In one embodiment of the multi-part device, one of said long side walls of said liquid waste container comprises a notch.

In one embodiment of the multi-part device, the support part comprises an enclosure, said enclosure being configured to receive the liquid waste container.

In one embodiment of the multi-part device, said enclosure comprises opposing short side walls and two opposing long side walls.

In one embodiment of the multi-part device, one of said long side walls of the enclosure comprises a ridge, said ridge being configured to align with the notch of one of the long side walls of the liquid waste container. In a further embodiment, the multiwell plate comprises two short and two long side walls and a rim extending around the circumference of the plate. In one embodiment, the rim and one short side wall together comprise a circular opening which aligns with the notch of the enclosure and the notch of the liquid waste container. This ensures proper loading the multi-part device on the separation station, which comprises a pin which interacts with the opening when the multi-part device is loaded on the separation station.

In one embodiment of the multi-part device, the device comprises two handles arranged on two opposing sides of said device. In a more specific embodiment, the two handles are arranged on the two longer side walls of the support part.

In one embodiment of the multi-part device, the device is manufactured as one single part. This provides stability to the device.

In one embodiment of the multi-part device, the device is made of plastic.

In one embodiment of the multi-part device, the device comprises an extension configured to receive a barcode. By this, it is possible to attach a bar code to the device itself. The barcode can be used to check for the presence of the device to ensure that the separation is not started in the absence of the device.

In one embodiment of the multi-part device, said enclosure of said device is integrally formed, wherein said enclosure comprises a closed bottom and an open top.

In one embodiment of the multi-part device, the multiwell comprises a base, wherein at least one row of vessels and one row of openings are formed within said base, wherein the openings are formed as funnels on the bottom side of said base, and wherein said funnels are extending into said liquid waste container.

The multi-part device and the liquid waste container permit the user to more easily and safely unload the consumables and the liquid waste after performing a magnetic separation.

The present disclosure also relates to a magnetic separation and heating system comprising a separation and incubation station and a multi-part device mounted on said separation and incubation station, said magnetic separation station comprising rows of magnets, wherein said magnets are configured to align with at least one row of vessels comprised in said multi-part device, wherein said multi-part device further comprises a support part configured to receive a tip holder, a liquid waste container and a multiwell plate, and wherein said tip holder and said liquid waste container are not contacted by said at least one row of magnets.

With this magnetic separation and incubation station it is possible to separate magnetic particles present in a vessel from the liquid component present in the same vessel.

In one embodiment, the multi-part device is as described herein.

In one embodiment of the magnetic separation and heating system, the separation station comprises a frame configured to receive the multi-part device.

In one embodiment, separation and incubation station are integrally formed. For example, different parts are fixed to each other in order to form an integrally formed part. Or the separation and incubation station may be molded as one part to form an integrally formed part. Thus, it is not necessary to transfer the multi-part device between a separation and heating station. This saves time and decreases the risk of contamination. In a more specific embodiment, the separation and incubation station comprises an incubator block configured to physically contact at least one row of vessels of the multiwell plate such that heat transfer is optimal.

In one embodiment, the magnetic separation and heating system additionally comprises a liquid transfer system. Said liquid transfer system may comprise a multipipetting device. This permits removal of liquid during separation, and addition of fresh liquids, e.g. for washing during separation.

The present disclosure further relates to a method of assembling a multi-part device comprising a device comprising a support part. The support part is configured to receive a tip holder, a liquid waste container and a multiwell plate. The multiwell plate comprises at least one row of vessels and one row of openings. The vessels comprise a closed bottom and an open top, and the openings are aligned with the liquid waste container when the liquid waste container and the multiwell plate are mounted on the support. The method comprises mounting the liquid waste container in the device and mounting the tip holder in the device. The liquid waste container and said tip holder can be mounted in any order, and, after mounting the liquid waste container, the multiwell plate is mounted on said device.

The present disclosure also relates to a system comprising a magnetic separation and heating station and a barcode reader, said barcode reader being configured to detect a barcode mounted on a device which is loaded on said magnetic separation and heating station.

In one embodiment, the system additionally comprises a device which is loaded on said magnetic separation and heating station, wherein the device comprises said barcode, and a computer controller configured to detect the presence of said device by reading said barcode with said barcode reader. The computer controller may further control the method of separating an analyte as described herein.

The present disclosure further relates to a magnetic separation and incubation station comprising a holder for receiving sample vessels. The movable magnets are connected to an actuator. The actuator is configured to move the movable magnets into proximity or away from the vessels. The magnetic separation and incubation station further comprises a heat block. The heat block is configured to contact the vessels to transfer heat to the contents of the vessels. Furthermore, a container is integrally formed with said magnetic separation and heating station. The container comprises a closed bottom, side walls and an open top. The container is configured to receive a pipette tip holder. Advantages of this magnetic separation and incubation station are as described herein.

In one embodiment, the magnetic separation and incubation station additionally comprises an open space configured to receive a liquid waste container. In a specific embodiment, the magnetic separation and incubation station is configured to receive a multi-part device as described herein.

The present disclosure further relates to a method of removing liquid waste during magnetic separation of an analyte. The method comprises Providing a device as described herein, a tip holder, a liquid waste container and a multiwell plate comprising liquid samples mounted on said device, to a magnetic separation station Providing magnetic particles to said sample Binding said analyte, if present in said sample, to said magnetic particles Separating said magnetic particles and said liquid samples using magnetic separation Removing said liquid sample by transferring said liquid sample to said liquid waste container using a liquid transfer system, thereby removing liquid waste during magnetic separation.

In one embodiment of the method, the analyte is a nucleic acid analyte.

In one embodiment of the method, the liquid waste is removed by removing the device from the magnetic separation station, and, thereafter, removing the liquid waste container, and discarding the liquid waste.

In one embodiment, the device is comprised in a multi-part device. The multi-part device comprises said device, the liquid waste container, the tip holder and the multiwell plate. The liquid waste is removed by removing the multi-part device from the magnetic separation station.

In one embodiment of the method, the device is re-useable.

In one embodiment, the multi-part device is grabbed manually by holding parts of the device and is, thus, unloaded from the separation and incubation station. After discarding the multiwell plate and the tip holder comprising the used tips, the liquid waste container can be removed from the device and the liquid waste can be discarded. This ensures easy and safe removal of all used consumables and liquid waste after magnetic separation in the system and, thus, reduces the risk of contamination or errors caused by consumables which were not properly unloaded from the system.

The present disclosure further relates to a method of separating an analyte using magnetic separation, comprising the steps of Providing a device as described herein, a liquid waste container, a tip holder and a multiwell plate comprising liquid samples mounted on said device, to a magnetic separation station Providing magnetic particles to said sample Binding said analyte, if present in said sample, to said magnetic particles Separating said magnetic particles and said liquid samples using magnetic separation wherein, after said separation, the device is removed from said magnetic separation station, the liquid waste container is removed and the liquid waste discarded, and the multiwell plate is removed and discarded, and wherein the device is re-used.

In one embodiment of the method, the device is cleaned before re-use.

EXAMPLES

Figure 1B:
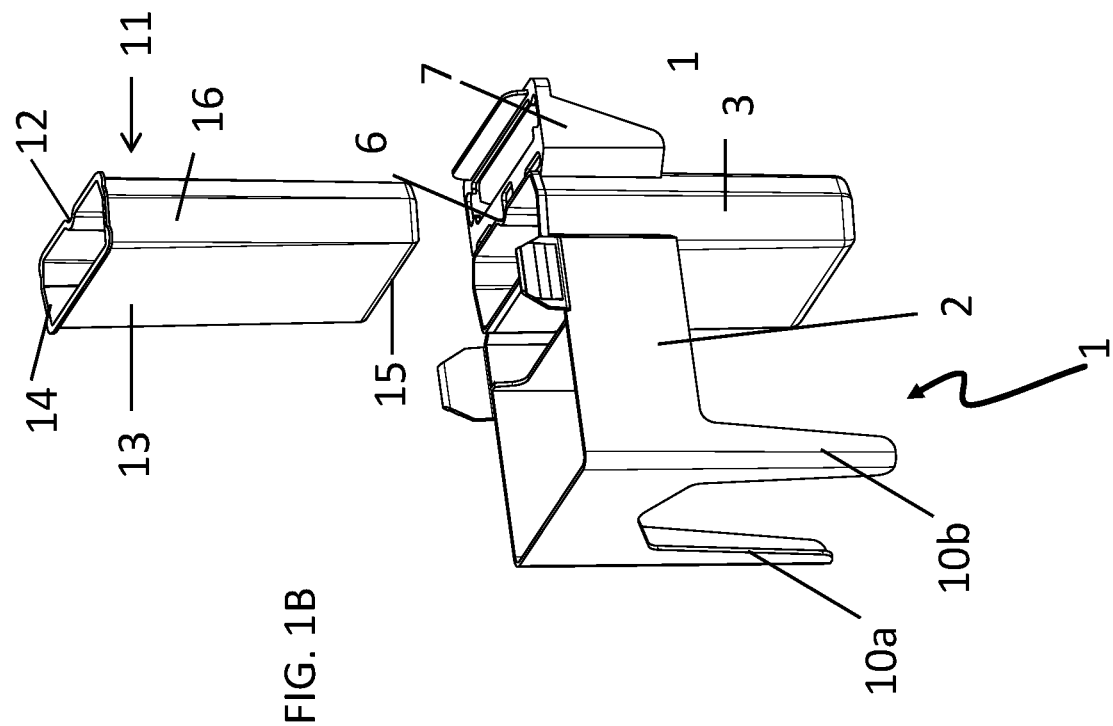

In FIG. 1A, a device (1) is shown. The device (1) comprises support part (2). The support part (2) further comprises an enclosure (3). The enclosure (3) comprises opposing short side walls (4a, 4b) and opposing long side walls (5a, 5b). As shown in FIG. 1A, one of said long side walls (5b) comprises a ridge (6). Also shown in FIG. 1B is a liquid waste container (11). The support part further comprises a holding part (7) for receiving and holding a tip holder. Also shown in FIG. 1A are two handles (8a, 8b). The support part also comprises an extension (9) on which a barcode may be attached. The support part comprises legs (10a, b) which provide stability to the device (1) and make sure the items loaded on the device (1) are level. The liquid waste container (11) comprises short side walls (16) and long side walls (13), and an opening (14) on the top, while the bottom (15) is closed.

Figure 1C:
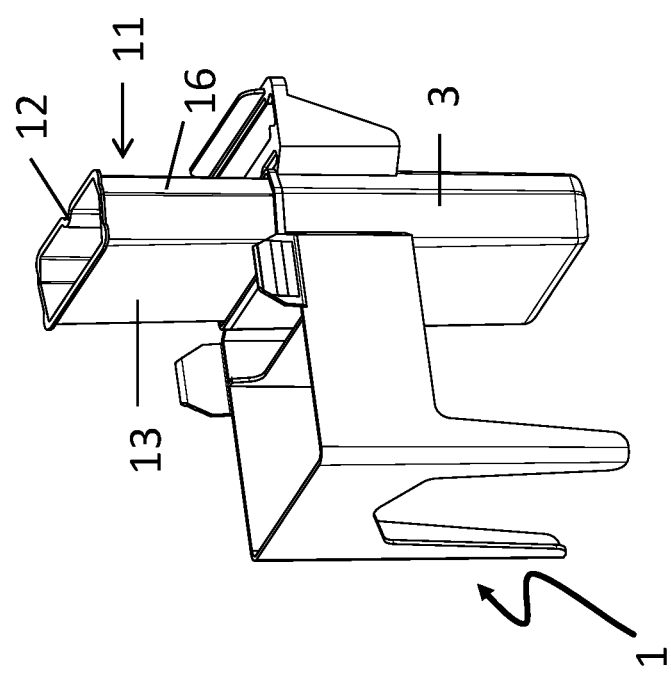
Figure 1D:
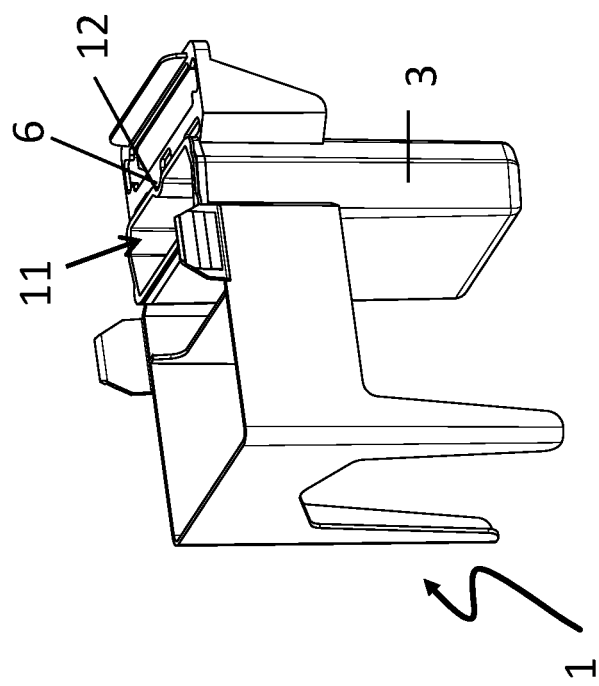

FIGS. 1B to 1D illustrate different states of loading a liquid waste container (11) on the device (1). In FIG. 1B, the liquid waste container (11) is located above the enclosure (3). The liquid waste container (11) has notch (12) which aligns with ridge (6) of the enclosure (3) when the liquid waste container (11) is loaded. In FIG. 1C, the liquid waste container (11) is partially loaded into the enclosure (3). In FIG. 1D, the liquid waste container (11) is completely loaded into the enclosure (3).

Figure 2:
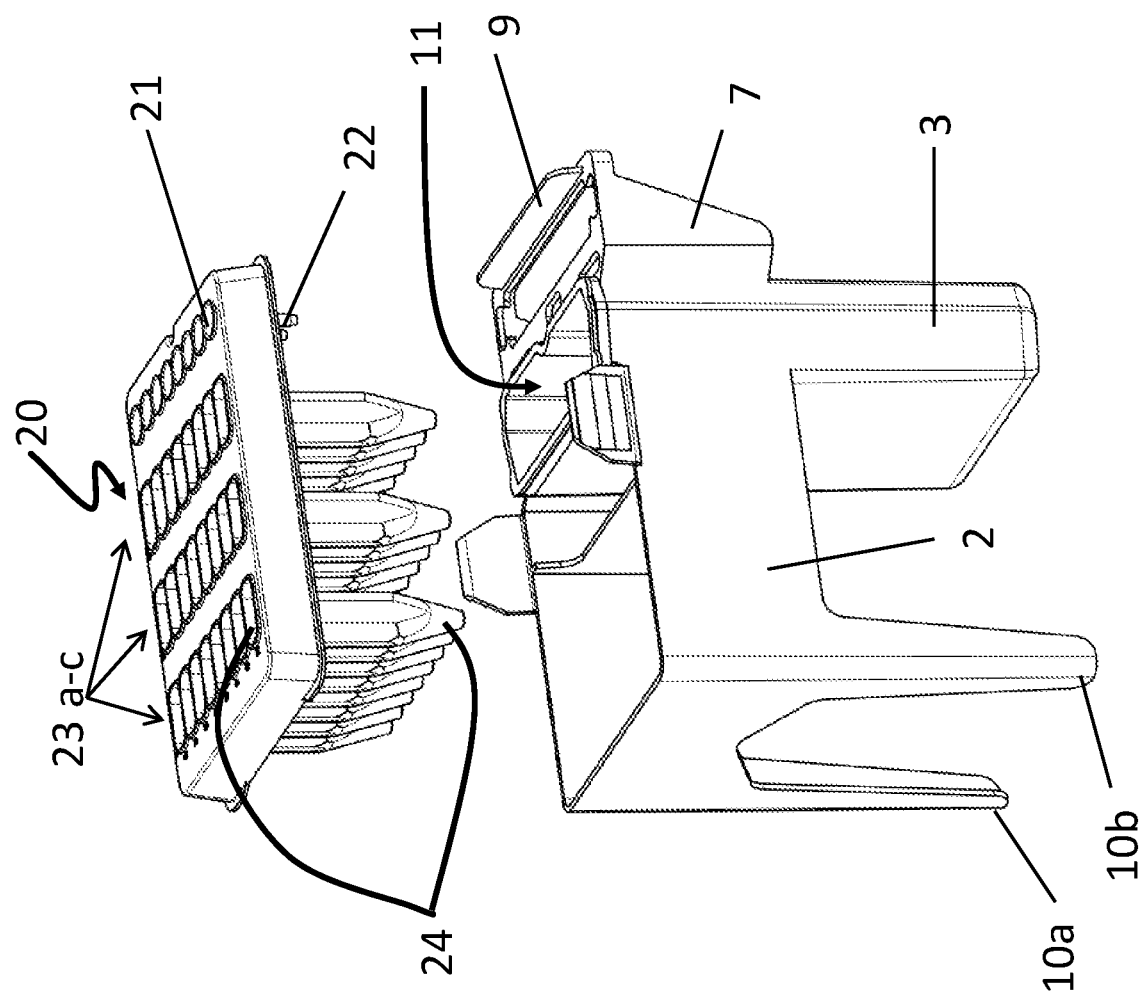
FIG. 2 shows how the multiwell plate (20) is loaded onto the support part (2) of the device (1).
Figure 3:
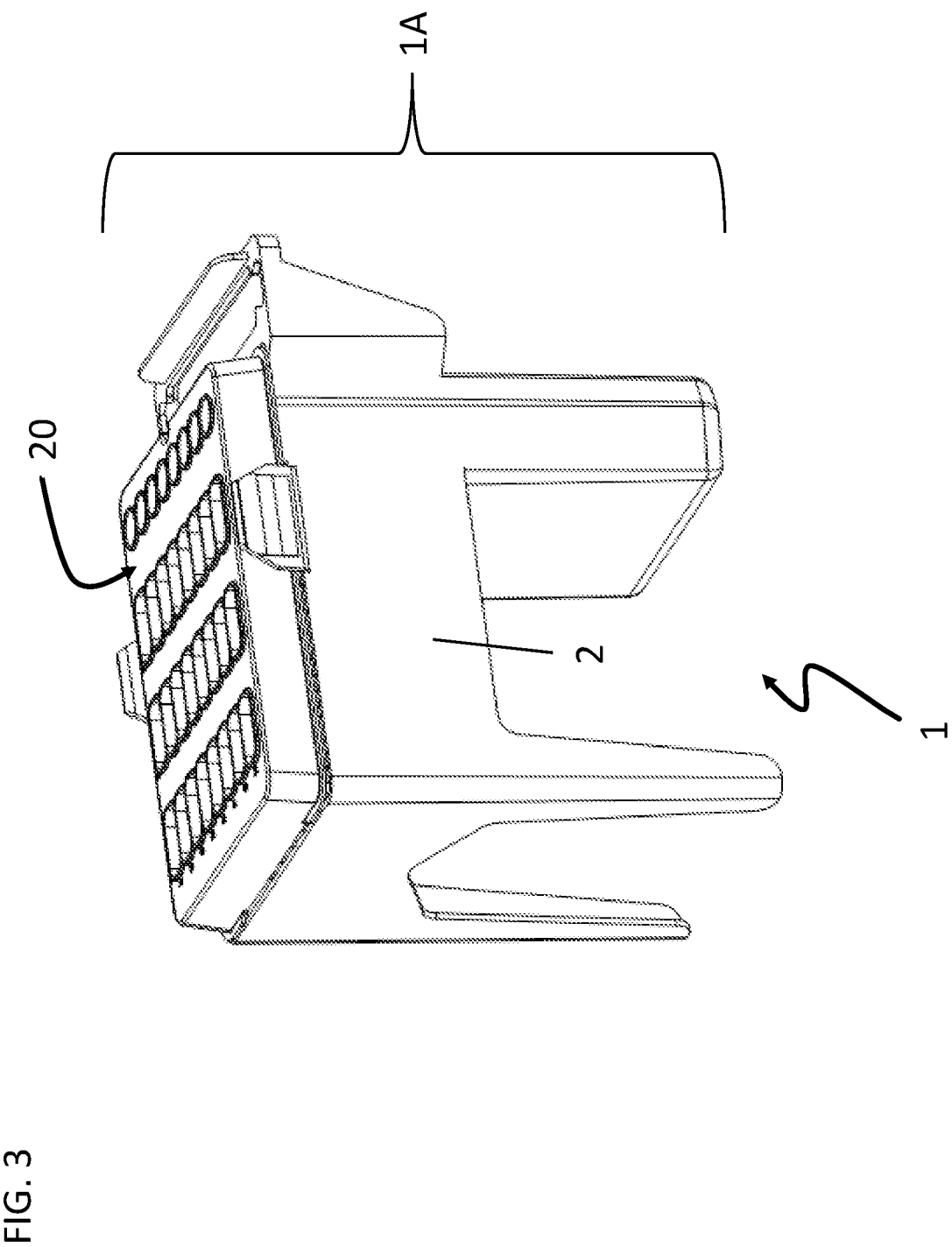
FIG. 3 shows the device (1) with a loaded liquid waste container (11) (not visible) and multiwell plate (20).
Figure 4:
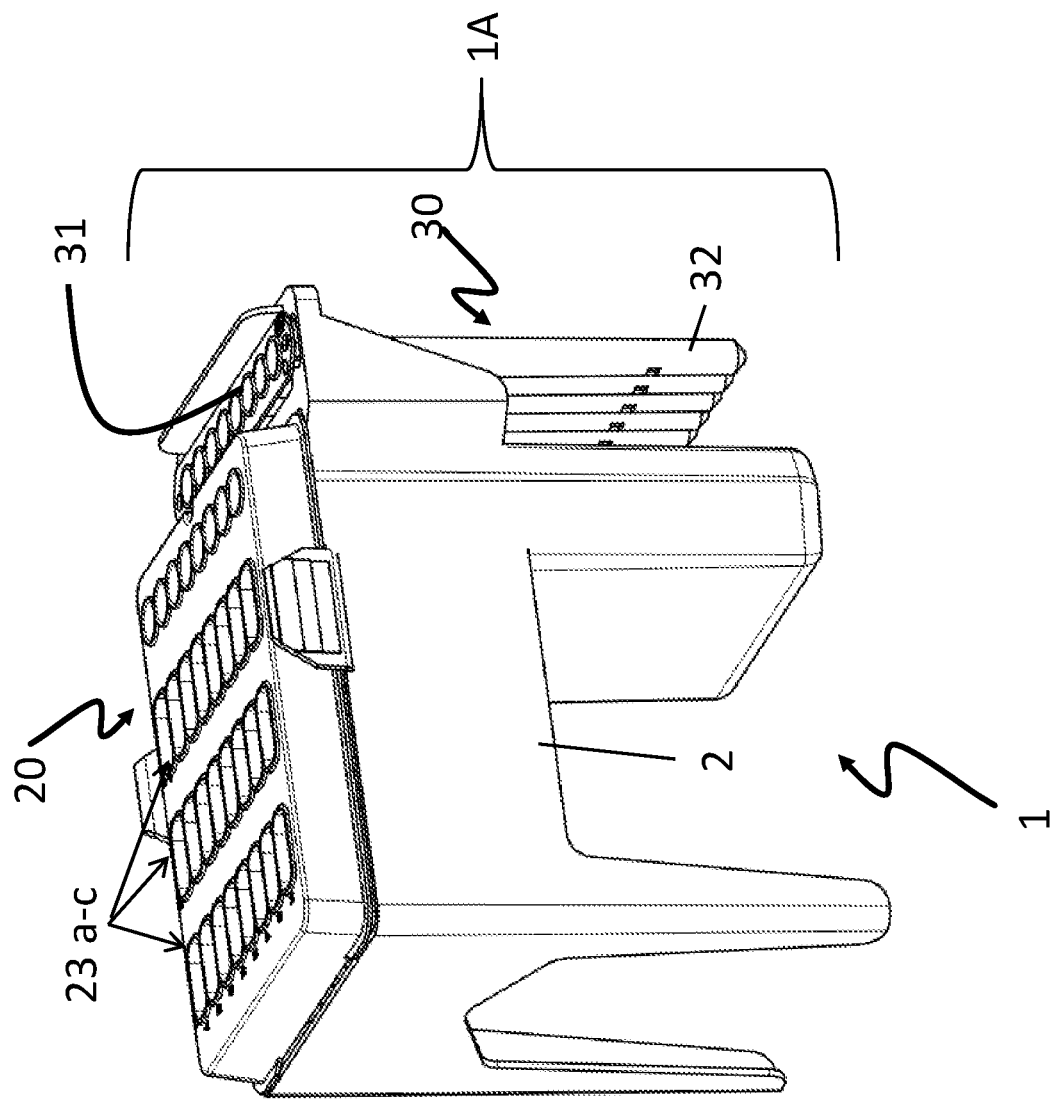
FIG. 4 shows the multi-part device (1A) with additionally loaded tip holder (30).

FIG. 2 shows how the multiwell plate (20) is loaded onto the support part (2) of the device (1). The multiwell plate (20) is loaded after the liquid waste container (11). The multiwell plate comprises a row of openings (21) which align with the liquid waste container (11). The openings are used to discard liquid waste into liquid waste container (11). In the embodiment shown in this Figure, the openings (21) are formed as funnels (22). This prevents splashing of liquid waste. The multiwell plate shown in FIG. 2 has three rows (23a to c) of vessels (24), each row comprising 8 vessels, and one row of openings (21). FIG. 3 shows the device (1) with a loaded liquid waste container (11) (not visible) and multiwell plate (20). A device comprising a loaded multiwell plate (20) and liquid waste container (11) is referred to as multi-part device (1A). FIG. 4 shows the multi-part device (1A) with additionally loaded tip holder (30) comprising a row of tip holder vessels (32) each holding one tip (31). In the embodiment shown in FIG. 4, the number of tips (31) is equal to the number of vessels (24) in one row (23a, b or c).

FIGS. 5A and 5B show in the upper part the multi-part device (1A), in FIG. 5A, loaded with the liquid waste container (11) (not visible) and multiwell plate (20), and in FIG. 5B, loaded additionally with tip holder (30) comprising tip holder vessels (32) and tips (31). In the lower part of each of the two Figures, an exemplary separation and heating station (40) is shown. The magnetic separation and incubation station (40) comprises a holder for receiving sample vessels. Movable magnets (42) are connected to an actuator (43). The actuator (43) is configured to move the movable magnets (42) into proximity or away from the vessels (24). The magnetic separation and incubation station (40) further comprises a heat block (44). The heat block (44) is configured to contact the vessels (24) to transfer heat to the contents of the vessels (24). Furthermore, a container (45) is integrally formed with said magnetic separation and heating station (40). The container (45) comprises a closed bottom (46), side walls (47) and an open top (48). The container is configured to receive a pipette tip holder (32). The multipart device (1A) can be loaded on the separation and incubation station (40) either without the tips (31) in the tip holder (39), as shown in FIG. 5a) and FIG. 6, or with the tips (31) in the tip holder (30) pre-loaded, as in FIG. 5b). Also shown is a pin (41) with which ridge (6) and notch (12) align.

Figures 6C, 6D:
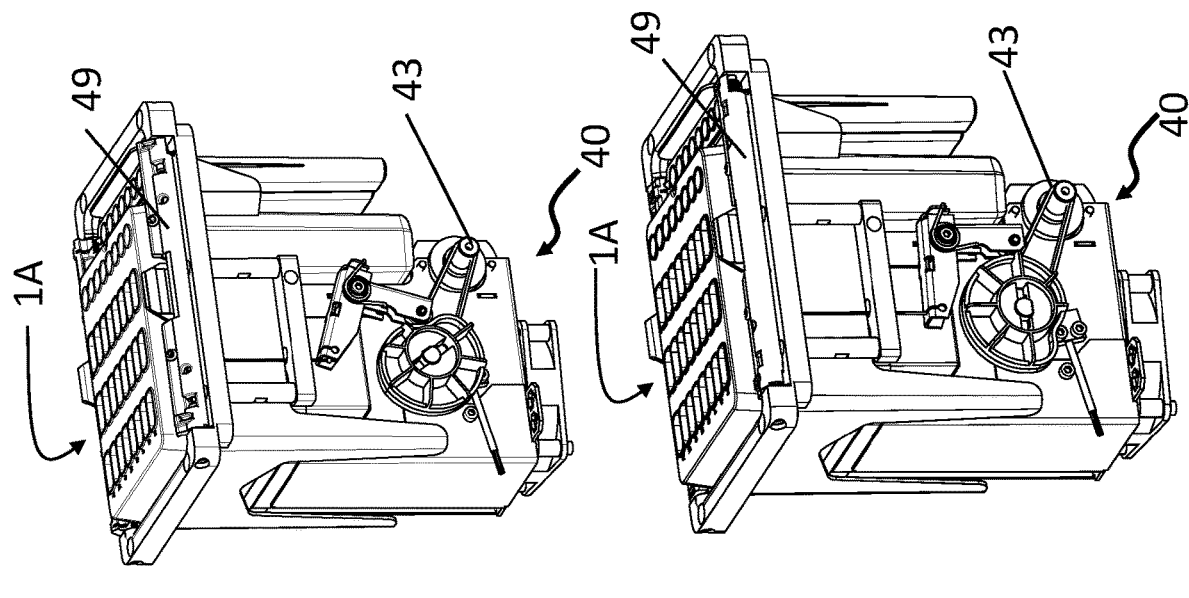

FIGS. 6A to 6D show different stages of loading of the multi-part device (1A) into the separation and incubation station (40). In FIG. 6A, the multi-part device (1A) is loaded onto the separation station (40) without the tip holder (30). In FIG. 6B, the tip holder (30) comprising tips (31) is loaded into the device (1) and container (45). The separation and incubation station (40) comprises a downholding mechanism (49) which is open in FIGS. 6A to 6C. When the multi-part device (1A) is completely loaded, the downholding mechanism (49) is moved into a locked position, shown in FIG. 6D, which downholds the multipart device (1A) in the separation and incubation station (40). This ensures that the multipart device (1A) stays in place during magnetic separation. The closing and opening is mediated by actuator (43).

FIG. 7 shows the device 1 after discarding the multiwell plate (20) and tip holder (30). The liquid waste container (11) can be easily removed and the contents discarded.

Figure 8:
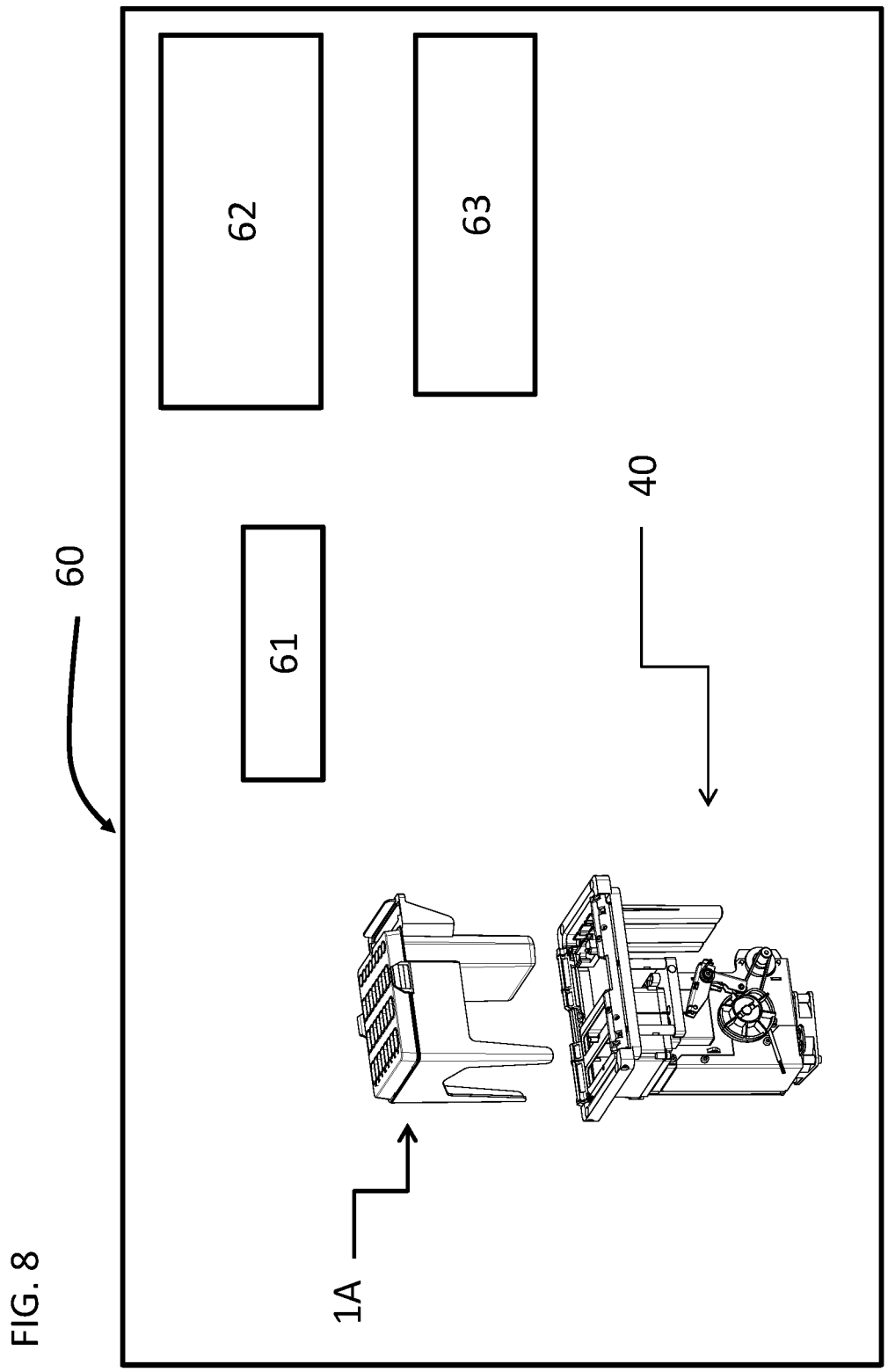
FIG. 8 shows a system (60) comprising a magnetic separation and incubation station (40) and a barcode reader (61). The system further comprises a computer controller (62) and a multi-pipetting device (63).

FIG. 8 shows a system (60) comprising a magnetic separation and incubation station (40) and a barcode reader (61). The system further comprises a computer controller (62). Further, the system comprises a multi-pipetting device (63).

The present application is not to be limited in scope by the specific embodiments described herein. Indeed, various modifications in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A multi-part device comprising:
   (a) a tip holder;
   (b) a multiwell plate comprising at least one row of vessels, each vessel in the at least one row of vessels comprising a closed bottom and an open top;
   (c) a liquid waste container, wherein the liquid waste container has opposing long side walls and opposing short side walls, which encompass an inner volume, and wherein the liquid waste container comprises a closed bottom and an open top, and wherein one of the long side walls comprises a notch; and (d) a support part configured to receive the multiwell plate, and wherein the support part includes:
   (i) an enclosure configured to receive the liquid waste container, wherein the enclosure comprises opposing short side walls and two opposing long side walls, wherein one of the long side walls comprises a ridge, the ridge being configured to align with the notch of one of the long side walls of the liquid waste container, and
   (ii) a holding part configured to receive the tip holder, and wherein alignment of the notch of the liquid waste container with the ridge of the enclosure of the support part ensures proper alignment of the liquid waste container and the support part.

2. The device of claim 1, wherein the tip holder comprises one row of individually formed tip holder vessels configured to receive pipette tips, and wherein the number of tip holder vessels in the one row of individually formed tip holder vessels is equal to the number of vessels in the at least one row of vessels of the multiwell plate.

3. The device of claim 2, wherein the vessels in the at least one row of vessels and the tip holder vessels of the one row of individually formed tip holder vessels are aligned.

4. The device of claim 1, wherein the multiwell plate additionally comprises one row of openings, and the openings are located above the liquid waste container when the liquid waste container and the multiwell plate are mounted on the support.

5. The device of claim 1, wherein the enclosure comprises a closed bottom and an open top.

6. The device of claim 1, wherein the device is re-useable.

7. A method of removing liquid waste during magnetic separation of an analyte, comprising
   presenting a device according to claim 1, a liquid waste container and a multiwell plate comprising liquid samples mounted on the device to a magnetic separation station;
   introducing magnetic parties into the sample;
   binding the analyte, if present in the sample, to the magnetic particles;
   separating the magnetic particles and the liquid samples using magnetic separation; and
   removing the liquid sample by transferring the liquid sample to the liquid waste container using a liquid transfer system, thereby removing liquid waste during magnetic separation.

8. The method according to claim 7, wherein the analyte is a nucleic acid analyte.

9. The method of claim 7, wherein the liquid waste is removed by removing the device from the magnetic separation station, and thereafter, removing the liquid waste container, and discarding the liquid.

10. The method of claim 7, wherein the device is comprised in a multi-part device, the multi-part device comprises the device, the liquid waste container and the multiwell plate, and wherein the liquid waste is removed by removing the multi-part device from the magnetic separation station.

11. The method of claim 7, wherein the device is re-useable.

* * * * *